United States Patent
Naito et al.

(10) Patent No.: US 12,213,778 B2
(45) Date of Patent: Feb. 4, 2025

(54) MUSCLE ACTIVITY OBSERVATION APPARATUS AND MUSCLE ACTIVITY OBSERVATION METHOD

(71) Applicant: Murata Manufacturing Co., Ltd., Nagaokakyo (JP)

(72) Inventors: Atsushi Naito, Nagaokakyo (JP); Naoki Kawara, Nagaokakyo (JP); Yutaka Takamaru, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 808 days.

(21) Appl. No.: 17/316,048

(22) Filed: May 10, 2021

(65) Prior Publication Data

US 2021/0259581 A1    Aug. 26, 2021

Related U.S. Application Data

(63) Continuation of application No. PCT/JP2019/043786, filed on Nov. 8, 2019.

(30) Foreign Application Priority Data

Nov. 29, 2018    (JP) .................................. 2018-223761

(51) Int. Cl.
*A61B 5/11*    (2006.01)
*A61B 5/00*    (2006.01)
(Continued)

(52) U.S. Cl.
CPC .......... *A61B 5/1107* (2013.01); *A61B 5/1101* (2013.01); *A61B 5/224* (2013.01);
(Continued)

(58) Field of Classification Search
CPC ....... A61B 5/11; A61B 5/1101; A61B 5/1107; A61B 5/1114; A61B 5/1116–1126;
(Continued)

(56) References Cited

U.S. PATENT DOCUMENTS 2,594,841 A * 4/1952 Arndt, Jr. .................. H03F 1/36
                                                318/116
5,012,411 A * 4/1991 Policastro .............. G16H 40/67
                                                600/513
(Continued)

FOREIGN PATENT DOCUMENTS

JP    2005230367 A    9/2005
JP    2006305311 A    11/2006
(Continued)

OTHER PUBLICATIONS

Machine translation of WO 2016/027615 A1 (Year: 2016).*
(Continued)

*Primary Examiner* — David J. McCrosky
(74) *Attorney, Agent, or Firm* — ArentFox Schiff LLP

(57)    ABSTRACT

A muscle activity observation apparatus that includes a sensor module and a detection module. The sensor module includes a piezoelectric sensor. Moreover, the piezoelectric sensor has an output that changes in accordance with a tremor of a tendon or a muscle, and an output that changes in accordance with contraction and relaxation of the tendon or the muscle. A detector of the detection module detects an activity state of the tendon or the muscle using a tremor signal and a contraction-relaxation signal output from the piezoelectric sensor.

30 Claims, 12 Drawing Sheets

(51) Int. Cl.
  *A61B 5/22* (2006.01)
  *G01D 5/18* (2006.01)
  *G01L 1/16* (2006.01)
  *G16H 40/67* (2018.01)

(52) U.S. Cl.
  CPC .......... *A61B 5/6829* (2013.01); *A61B 5/7278* (2013.01); *G01D 5/185* (2021.05); *G01L 1/16* (2013.01); *G16H 40/67* (2018.01); *A61B 2560/0475* (2013.01); *A61B 2562/0204* (2013.01); *A61B 2562/0219* (2013.01); *A61B 2562/06* (2013.01)

(58) Field of Classification Search
  CPC ..... A61B 5/224; A61B 5/6829; A61B 5/7278; A61B 2560/0475; A61B 2562/0204; A61B 2562/0219; A61B 2562/06; G16H 40/67; Y10S 128/92; Y10S 128/923–925
  See application file for complete search history.

(56) References Cited

U.S. PATENT DOCUMENTS

| | | | |
|---|---|---|---|
| 2005/0113652 A1 | 5/2005 | Stark et al. | |
| 2011/0196262 A1* | 8/2011 | McLeod | A61B 5/224 600/587 |
| 2013/0324857 A1* | 12/2013 | Kurillo | A61B 5/1127 600/595 |
| 2015/0165269 A1* | 6/2015 | Herrala | A61B 5/296 482/8 |
| 2017/0055836 A1 | 3/2017 | Thelen et al. | |
| 2017/0215768 A1 | 8/2017 | Belfiori | |
| 2019/0003905 A1* | 1/2019 | Yoshida | H10N 30/30 |
| 2020/0058844 A1 | 2/2020 | Tanimoto et al. | |

FOREIGN PATENT DOCUMENTS

| | | | |
|---|---|---|---|
| JP | 2006345990 A | 12/2006 | |
| JP | 2008086392 A | 4/2008 | |
| JP | 2010029633 A | 2/2010 | |
| JP | 2015147038 A | 8/2015 | |
| JP | 2016127898 A | 7/2016 | |
| JP | 2016150178 A | 8/2016 | |
| JP | 2019162538 A | 9/2019 | |
| WO | WO-2016027615 A1 * | 2/2016 | .......... A61B 5/0245 |
| WO | 2018092886 A1 | 5/2018 | |

OTHER PUBLICATIONS

International Search Report issued for PCT/JP2019/043786, date of mailing Feb. 4, 2020.
Written Opinion of the International Searching Authority issued for PCT/JP2019/043786, date of mailing Feb. 4, 2020.
Beck, Travis W. et al.; "Comparison of a piezoelectric contact sensor and an accelerometer for examining mechanomyographic amplitude and mean power frequency versus torque relationships during isokinetic and isometric muscle actions of the biceps brachii"; Journal of Electromyography and Kinesiology, Aug. 31, 2006, vol. 16, No. 4, pp. 324-335.
May, E. L. et al.; "Application of a piezoelectric sensor for measuring shivering in a small marsupial"; Journal of Thermal Biology, Oct. 31, 2003, vol. 28, pp. 469-475.
Japanese Office Action issued for JP Application No. 2020-134324, date of dispatch Jun. 1, 2021.

* cited by examiner

| TYPE OF MUSCLE ACTIVITY | TREMOR SIGNAL | CONTRACTION-RELAXATION SIGNAL |
|---|---|---|
| ISOMETRIC CONTRACTION | AMPLITUDE: LARGE | NO AMPLITUDE CHANGE |
| ISOTONIC CONTRACTION | AMPLITUDE: LARGE | AMPLITUDE CHANGE |
| PASSIVE MOVEMENT | AMPLITUDE: SMALL | AMPLITUDE CHANGE |
| AT REST | AMPLITUDE: SMALL | NO AMPLITUDE CHANGE |

FIG. 18(A)

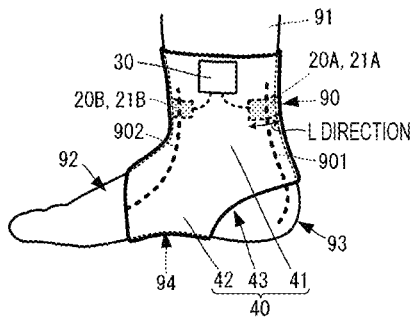

FIG. 18(B)

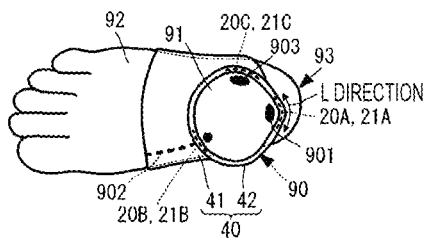

FIG. 19

| SITE | MOVEMENT | TENDON OR MUSCLE BEING OBSERVED |
|---|---|---|
| FOOT (LOWER LEG) | FLEXION (PLANTAR FLEXION) | TIBIALIS POSTERIOR TENDON (SOLEUS MUSCLE, GASTROCNEMIUS MUSCLE, etc.) |
| | EXTENSION (DORSIFLEXION) | TIBIALIS ANTERIOR MUSCLE TENDON (TIBIALIS ANTERIOR MUSCLE) |
| | INVERSION | TIBIALIS POSTERIOR TENDON (GASTROCNEMIUS MUSCLE) |
| | EVERSION | PERONEUS LONGUS MUSCLE TENDON (PERONEUS LONGUS MUSCLE) |
| KNEE (THIGH) | FLEXION | QUADRICEPS FEMORIS MUSCLE |
| | EXTENSION | HAMSTRINGS |
| HAND, FINGERS | FLEXION (PALM FLEXION) | PALMAR FLEXOR MUSCLES (FLEXOR DIGITORUM PROFUNDUS, FLEXOR DIGITORUM SUPERFICIALIS, FLEXOR POLLICIS LONGUS, etc.) |
| | EXTENSION (DORSIFLEXION) | PALMAR DORSIFLEXOR MUSCLES (EXTENSOR DIGITORUM, etc.) |
| ELBOW (UPPER ARM) | FLEXION | BICEPS |
| | EXTENSION | TRICEPS |
| ABDOMEN, LOWER BACK | FLEXION (SPINAL ANTEFLEXION) | RECTUS ABDOMINIS MUSCLE |
| | EXTENSION (SPINAL RETROFLEXION) | INTRINSIC BACK MUSCLES (ERECTOR SPINAE MUSCLES, etc.) |
| CHEST | FLEXION (CONTRACTION) | PECTORALIS MAJOR |
| | EXTENSION | LATISSIMUS DORSI | ns
MUSCLE ACTIVITY OBSERVATION APPARATUS AND MUSCLE ACTIVITY OBSERVATION METHOD

CROSS REFERENCE TO RELATED APPLICATIONS

The present application is a continuation of PCT/JP2019/043786 filed Nov. 8, 2019, which claims priority to JP Application No. 2018-223761, filed Nov. 29, 2018, the entire contents of each of which are incorporated herein by reference.

TECHNICAL FIELD

The present invention relates to the technology of muscle activity observation and detection for observing muscle activities.

BACKGROUND

A muscle movement detection apparatus described in Japanese Unexamined Patent Application Publication No. 2010-29633 (hereinafter "Patent Document 1") includes a sensor and a controller. The electric resistance of the sensor changes in accordance with contraction involved in muscle movement. The controller detects a voltage in accordance with muscle movement using the electric resistance of the sensor.

However, the muscle movement detection apparatus described in Patent Document 1 cannot distinguishably measure isotonic contraction and isometric contraction. It is thus difficult to accurately grasp muscle activities.

SUMMARY OF THE INVENTION

Thus, it is an object of the present invention to provide an apparatus and method for muscle activity observation and detection that distinguishably observes isotonic contraction and isometric contraction.

Accordingly, a muscle activity observation and detection apparatus is disclosed that includes a first sensor, a second sensor, and a detector. The first sensor generates an output signal that changes in accordance with a tremor of a tendon or a muscle. The second sensor generates an output signal that changes in accordance with contraction and relaxation of the tendon or the muscle. Moreover, the detector detects an activity state of the tendon or the muscle using an output signal of the first sensor and an output signal of the second sensor.

In this configuration, a signal based on a tremor of the tendon or the muscle (e.g., a tremor signal) is obtained by the first sensor. In addition, a signal based on contraction and relaxation of the tendon or the muscle (e.g., a contraction-relaxation signal) is obtained by the second sensor. Because the tremor signal and the contraction-relaxation signal are individually obtained, the state of isometric contraction and the state of isotonic contraction are individually identifiable.

According to the exemplary embodiment of the present invention, isotonic contraction and isometric contraction can be distinguishably observed. Accordingly, the activity and the state of a tendon or a muscle is more accurately determined than conventional systems and methods.

BRIEF DESCRIPTION OF DRAWINGS

FIG. 18(A) is a side view illustrating the state in which the muscle activity observation apparatus is attached to a foot, and FIG. 18(B) is a plan view illustrating the state in which the muscle activity observation apparatus is attached to the foot.

FIG. 19 is a table illustrating an example of the relationship among a site, a movement, and a tendon or a muscle being observed.

DETAILED DESCRIPTION OF EMBODIMENTS

First Exemplary Embodiment

Figure 1:
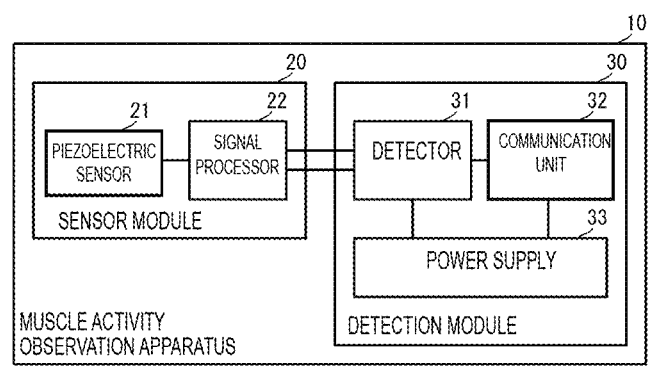
FIG. 1 is a block diagram illustrating the configuration of a muscle activity observation apparatus according to a first exemplary embodiment.

A muscle activity observation and detection apparatus according to a first exemplary embodiment will be described with reference to the drawings. FIG. 1 is a block diagram illustrating the configuration of the muscle activity observation and detection apparatus according to the first exemplary embodiment. In general, the terms observation and detection are used synonymously.

(Configuration of Functional Blocks of Muscle Activity Observation Apparatus)

As illustrated in FIG. 1, a muscle activity observation apparatus 10 includes a sensor module 20 and a detection module 30. The sensor module 20 includes a piezoelectric sensor 21 and a signal processor 22. The detection module 30 includes a detector 31, a communication unit 32, and a power supply 33.

According to the exemplary aspect, the piezoelectric sensor 21 is displaced in accordance with the activity of a tendon or a muscle of a living body. A piezoelectric body 201 generates electric charge (potential difference) in accordance with this displacement. The signal processor 22 is configured to convert electric charge detected by the piezoelectric sensor 21 to a voltage signal, thereby generating a tremor signal and a contraction-relaxation signal. The signal processor 22 outputs the tremor signal and the contraction-relaxation signal to the detector 31.

The detector 31 is configured to detect a tremor state from the tremor signal, and detect a contraction-relaxation state from the contraction-relaxation signal. In addition, the detector 31 analyzes the movement of a site being observed (such as a foot) of the living body from the tremor state and the contraction-relaxation state.

It is noted that tremors in the present disclosure are considered to be involuntary movements that represent rhythmic muscle activities. That is, tremors in the present application are fine and fast postural tremors observed in normal people, and are referred to as physiological tremors, which have frequencies from 8 Hz to 12 Hz, for example. Moreover, it is noted that tremors observed in patients with Parkinson's disease and other illnesses are pathological tremors, which have frequencies from 4 Hz to 7 Hz, for example, and which do not serve as tremors in the present disclosure.

The use of tremors has various advantages as follows over myoelectricity. For example, detection (detector) of a tremor may be performed without directly attaching a sensor to the surface (such as skin) of a to-be-detected body such as a human body. Muscle contraction and relaxation may be detected by detecting a tremor. Moreover, a change involved in muscle fatigue can be detected by detecting a tremor.

The communication unit 32 is configured to communicate the results of detecting a tremor state, a contraction-relaxation state, the movement of the site of the living body being observed, and so forth to the outside. The communication method may be wireless or wired. The power supply 33 supplies electric power to the detector 31 and the communication unit 32. Note that the power supply 33 may additionally supply power to the signal processor 22 of the sensor module 20. However, the sensor module 20 can be provided with a power supply besides the power supply 33 according to alternative aspects.

(Exemplary Mode in which Muscle Activity Observation Apparatus is Attached)

In the exemplary aspect, the muscle activity observation apparatus 10 is attached to the above-mentioned site of the living body being observed by as follows, for example. Specifically, FIG. 2(A) is a side view illustrating the state in which the muscle activity observation apparatus is attached to a foot, and FIG. 2(B) is a plan view illustrating the state in which the muscle activity observation apparatus is attached to the foot.

Figure 2A:
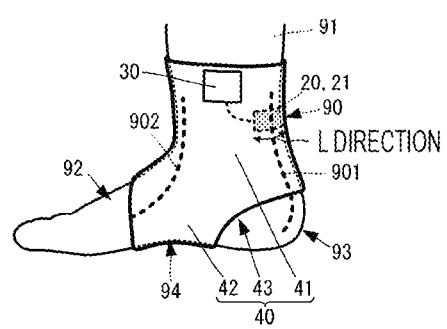
FIG. 2(A) is a side view illustrating the state in which the muscle activity observation apparatus is attached to a foot.
Figure 2B:
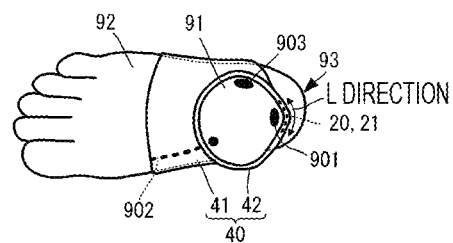
FIG. 2(B) is a plan view illustrating the state in which the muscle activity observation apparatus is attached to the foot.

As illustrated in FIGS. 2(A) and 2(B), the muscle activity observation apparatus 10 includes a living body support 40. The living body support 40 (or simply a "support") is made of a stretchable material and deforms in accordance with the movement of the living body. It is preferable that the living body support 40 be made of a material that does not inhibit the deformation of the piezoelectric sensor 21 (more specifically, the deformation of the piezoelectric body 201 of the piezoelectric sensor 21 (see FIG. 4)) as much as possible. For example, a cotton and acrylic blend, a polyester and cotton blend, a cotton and linen blend, an acrylic and wool blend, a wool and nylon blend, a fur blend, silk, spun silk, silk tussah (tussah spun silk), or the like may be used.

As shown, the living body support 40 includes a first portion 41 and a second portion 42. The first portion 41 and the second portion 42 are tubular and are connected in an approximately L-shape as viewed from the side. Moreover, the joint between the first portion 41 and the second portion 42 has a hole 43, which penetrates through the tubular hollow space to the outside.

As illustrated in FIG. 2(A) and FIG. 2(B), the living body support 40 is attached in accordance with the outer shape of the living body (e.g., a human body) near a heel 93 of the foot including tendons and muscles. On this occasion, the first portion 41 covers an ankle 91. The second portion 42 covers an instep 92 and a sole 94 of the foot. The heel 93 is exposed to the outside from the hole 43.

The piezoelectric sensor 21 is attached to the first portion 41. More specifically, the piezoelectric sensor 21 is attached to the first portion 41 by, for example, being attached with an adhesive to the first portion 41, being sewn to the first portion 41, or being accommodated in a pocket of the first portion 41. In the exemplary aspect, it is preferable that the piezoelectric sensor 21 be attached inside (e.g., hollow side of) the first portion 41.

In addition, the piezoelectric sensor 21 is arranged or otherwise disposed at a position that overlaps an Achilles tendon 901 in the first portion 41. It is also preferable that the piezoelectric sensor 21 be arranged at a position that overlaps a minimum leg girth 90. When arranged at such a position, the piezoelectric sensor 21 improves the sensitivity of generation of electric charge caused by a tremor and contraction-relaxation of the Achilles tendon 901.

Furthermore, the length direction (i.e., the L direction) of the piezoelectric sensor 21 is approximately orthogonal to a direction in which the Achilles tendon 901 extends. In the piezoelectric sensor 21 with a structure indicated in FIGS. 3 and 4, which will be described later, displacement with respect to the length direction (L direction) is most likely to generate electric charge. Accordingly, the piezoelectric sensor 21 is able to detect contraction and relaxation of the Achilles tendon 901 with high sensitivity.

Here, the mode of detecting a tremor and contraction-relaxation of the Achilles tendon 901 has been discussed. However, in the case of detecting a tremor and contraction-relaxation of a tibialis anterior muscle tendon 902, it is only necessary to arrange the piezoelectric sensor 21 to overlap the tibialis anterior muscle tendon 902. In addition, in the case of detecting a tremor and contraction-relaxation of a peroneus longus muscle tendon 903, it is only necessary to arrange the piezoelectric sensor 21 to overlap the peroneus longus muscle tendon 903. On this occasion, it is preferable that the length direction (L direction) of the piezoelectric sensor 21 be orthogonal to a direction in which the tendon extends as much as possible.

In addition, because the living body support 40 supports the instep 92, the sole 94, and the ankle 91 of the foot and is bent in the middle, the positional relationship between the living body support 40 and the foot hardly changes. Therefore, the position of the piezoelectric sensor 21 hardly changes, and the position of the piezoelectric sensor 21 is hardly shifted with respect to a tendon (here, the Achilles tendon 901) whose tremor and contraction-relaxation are to be detected. Accordingly, the piezoelectric sensor 21 reliably detects a tremor and contraction-relaxation of a tendon being detected.

As further shown, the detection module 30 is attached to the living body support 40. The detection module 30 can be attached to any position of the living body support 40. However, it is preferable that the attachment position of the detection module 30 be a position in an environment where it is easy to communicate with the outside. For example, the attachment position of the detection module 30 is outside the first portion 41 and near an end portion opposite to a side connected to the second portion 42 in a tubular extending direction. Note that the detection module 30 and the sensor module 20 are connected by a certain cable.

(Structure of Sensor Module 20)

Figure 3A:
FIG. 3(A) is a side view illustrating a schematic configuration of a sensor module.
Figure 3B:
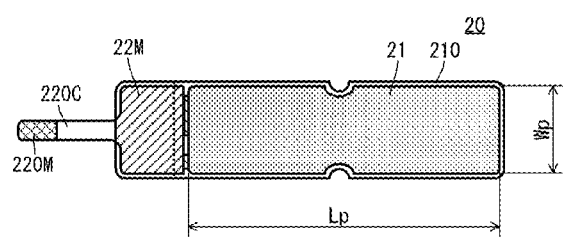
FIG. 3(B) is a plan view illustrating a schematic configuration of the sensor module.

FIG. 3(A) is a side view illustrating a schematic configuration of the sensor module, and FIG. 3(B) is a plan view illustrating a schematic configuration of the sensor module.

As illustrated in FIG. 3(A) and FIG. 3(B), the sensor module 20 is shaped as a flat film. The sensor module 20 includes the flat-film-shaped piezoelectric sensor 21, a thin signal processing circuit module 22M, a flat-film-shaped transmission cable 220C, and a connection terminal 220M.

The piezoelectric sensor 21 is shaped as an approximate rectangle with a length Lp and a width Wp. The length Lp is greater than the width Wp (Lp>Wp). The signal processing circuit module 22M is formed of an electronic component and a substrate configuring the signal processor 22, and the structure of a specific electronic component and the like is omitted in FIG. 3(A) and FIG. 3(B). The signal processing circuit module 22M is arranged side by side with the piezoelectric sensor 21, and is connected to the piezoelectric sensor 21 by a flat cable or the like. One of two ends in an extending direction of the transmission cable 220C is connected to the signal processing circuit module 22M. At the other end in the extending direction of the transmission cable 220C, the connection terminal 220M, which is made of a conductor, is formed.

(Structure and Output Signal of Piezoelectric Sensor 21)

Figure 4:
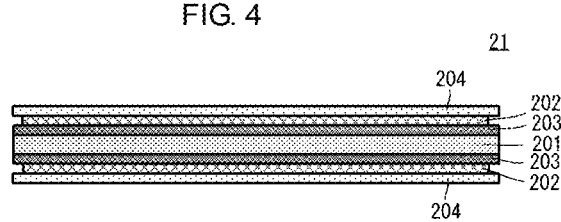
FIG. 4 is a cross-sectional side view illustrating a schematic configuration of a piezoelectric sensor.

FIG. 4 is a cross-sectional side view illustrating a schematic configuration of the piezoelectric sensor. As illustrated in FIG. 4, the piezoelectric sensor 21 includes the piezoelectric body 201, detection electrodes 202, adhesion layers 203 therebetween, and auxiliary plates 204.

Moreover, the piezoelectric body 201 is a rectangular film with main surfaces according to an exemplary aspect. For example, the length Lp of the piezoelectric body 201 is about 40 mm, the width Wp is about 10 mm, and the thickness is less than 0.3 mm. Note that the dimensions of the piezoelectric body 201 are not limited to these, and may be appropriately set in accordance with a target being observed. The piezoelectric body 201 is made of, for example, a material whose main component is polylactic acid (PLLA) or a material whose main component is aluminum nitride (AlN).

The detection electrodes 202 are adhered to the two main surfaces of the piezoelectric body 201 using the adhesion layers 203. It is preferable that the detection electrodes 202 be made of a highly conductive material such as copper (Cu). It is preferable that the adhesion layers 203 be as thin as possible.

The auxiliary plates 204 are arranged on the side of the detection electrodes 202 opposite the piezoelectric body 201. On this occasion, the main surfaces of the auxiliary plate 204 and the main surfaces of the piezoelectric body 201 are parallel.

Figure 5:
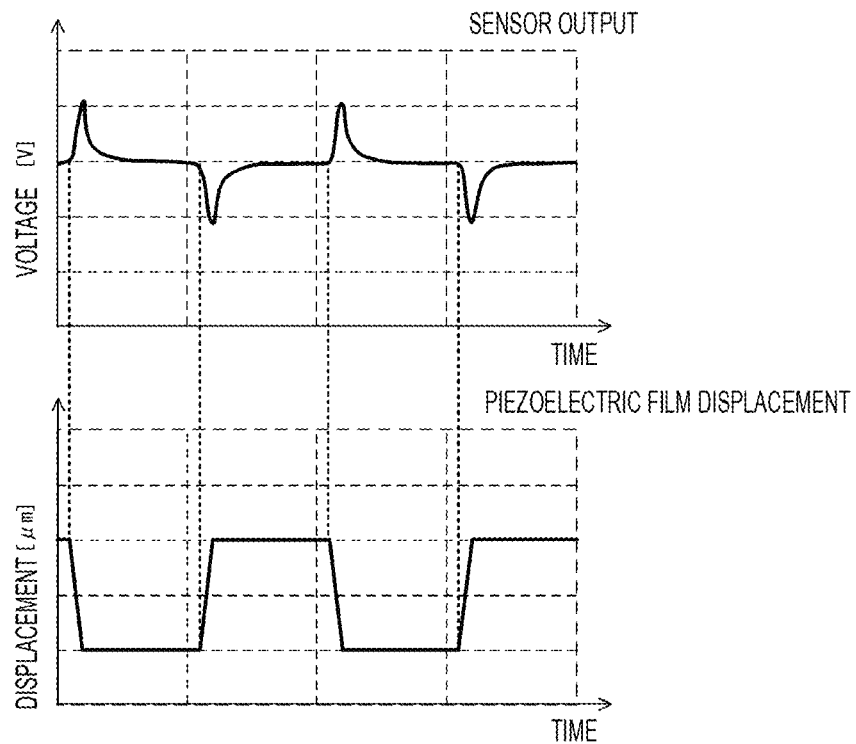
FIG. 5 is a waveform diagram illustrating an example of an output voltage of the piezoelectric sensor.

In such a configuration, if, for example, bending displacement in a direction orthogonal to the main surfaces of the piezoelectric body 201 occurs, electric charge with inverse characteristics is generated on the two detection electrodes 202. Due to the electric charge amount, a voltage such as that illustrated in FIG. 5 is generated across the two detection electrodes 202. FIG. 5 is a graph illustrating the relationship between bending displacement and voltage of the piezoelectric body 201. By detecting the voltage, that is, the electric charge amount, of the piezoelectric sensor 21 as described above, the bending displacement of the piezoelectric sensor 21 may be detected.

As illustrated in FIG. 2 described above, with the arrangement and configuration of the piezoelectric sensor 21, bending displacement occurs in the piezoelectric sensor 21 due to deformation of the attachment surface of the piezoelectric sensor 21, which is caused by contraction and relaxation of the Achilles tendon 901. Therefore, contraction and relaxation of the Achilles tendon 901 can be detected by detecting the voltage of the piezoelectric sensor 21.

Furthermore, the piezoelectric body 201 of the piezoelectric sensor 21 also generates electric charge even from a minute tremor. By detecting the voltage of the piezoelectric sensor 21, not only contraction and relaxation of the Achilles tendon 901, but also a tremor of the Achilles tendon 901 may be detected. Accordingly, a sensor for detecting contraction and relaxation of a tendon or a muscle and a sensor for detecting a tremor of a tendon or a muscle need not be individually provided. As a result, a sensor constructed for detecting contraction-relaxation and a tremor of a tendon or a muscle is provided with a simple configuration.

In addition, it is preferable for the auxiliary plates 204 to have the following characteristics. The auxiliary plates 204 only need to be harder than the piezoelectric body 201. Here, hardness is an index that represents the difficulty of bending. For example, the flexural modulus of the auxiliary plates 204 is higher than the flexural modulus of the piezoelectric body 201. As another index, if the piezoelectric body 201 is made of the above-mentioned material, the Young's modulus of the auxiliary plates 204 is preferably about 4 GPa. On this occasion, it is only necessary to set the flexural modulus or the Young's modulus of the auxiliary plates 204 so that the amount of electric charge generated for the same tremor magnitude be greater in the mode in which the auxiliary plates 204 are used than in the mode in which the auxiliary plates 204 are not used, but only the piezoelectric body 201 is used.

Accordingly, the piezoelectric sensor 21 is able to detect a tremor of the Achilles tendon 901 with high sensitivity.

(Configuration and Processing of Signal Processor 22)

Figure 6:
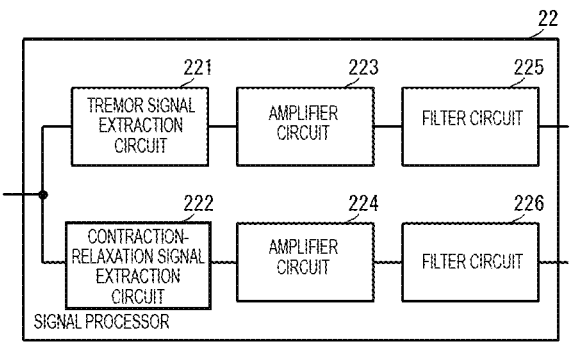
FIG. 6 is a block diagram illustrating the configuration of a signal processor.

FIG. 6 is a block diagram illustrating the configuration of the signal processor. As illustrated in FIG. 6, the signal processor 22 includes a tremor signal extraction circuit 221, a contraction-relaxation signal extraction circuit 222, an amplifier circuit 223, an amplifier circuit 224, a filter circuit 225, and a filter circuit 226.

The tremor signal extraction circuit 221 and the contraction-relaxation signal extraction circuit 222 are each configured of a charge amplifier circuit. On this occasion, the time constant of the charge amplifier of the tremor signal extraction circuit 221 is set for extracting a tremor signal. In addition, the time constant of the charge amplifier of the contraction-relaxation signal extraction circuit 222 is set for extracting a contraction-relaxation signal. For example, the time constant of the charge amplifier of the tremor signal extraction circuit 221 is less than the time constant of the charge amplifier of the contraction-relaxation signal extraction circuit 222.

Figure 7:
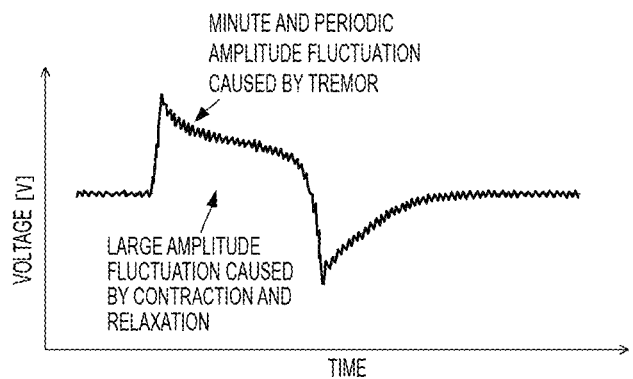
FIG. 7 is a waveform diagram for describing the concept of extracting a contraction-relaxation signal and a tremor signal.
Figure 8:
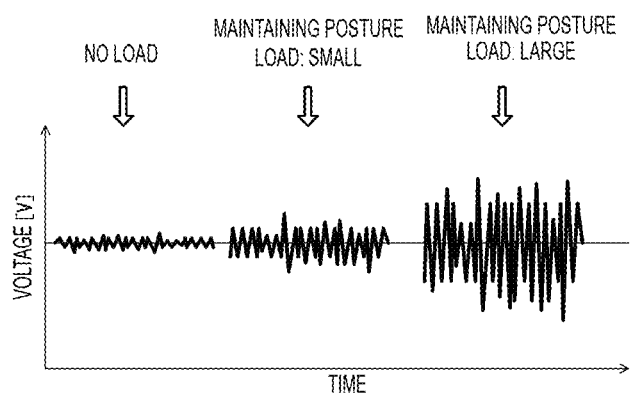
FIG. 8 is a waveform diagram illustrating an example of the waveform of a tremor signal.

FIG. 7 is a waveform diagram for describing the concept of extracting a contraction-relaxation signal and a tremor signal. In FIG. 7, time is on the abscissa and voltage is on the ordinate, and the case in which there is contraction and relaxation of a tendon is illustrated. FIG. 8 is a waveform diagram illustrating an example of the waveform of a tremor signal. The following description will also refer to, if necessary, the diagram of the output waveform of the piezoelectric sensor 21 illustrated in FIG. 5.

If a tendon contracts and relaxes, as illustrated in FIG. 5, the voltage fluctuates greatly. With the piezoelectric sensor 21 alone, the voltage fluctuation is temporary, as illustrated in FIG. 5. Here, voltage fluctuation caused by contraction and relaxation of a tendon can be output as an approximately square wave by appropriately setting the time constant of the contraction-relaxation signal extraction circuit 222, as illustrated in FIG. 7.

In addition, voltage fluctuation involved in a tremor of a tendon is small. However, voltage fluctuation involved in a tremor of a tendon has a frequency component of about 10 Hz. Therefore, minute and periodic voltage fluctuation caused by a tendon tremor may be output by appropriately setting the time constant of the tremor signal extraction circuit 221, as illustrated in FIG. 8.

A signal processed by the tremor signal extraction circuit 221 is input to the amplifier circuit 223. A signal processed by the contraction-relaxation signal extraction circuit 222 is input to the amplifier circuit 224.

The amplifier circuit 223 amplifies an output signal of the tremor signal extraction circuit 221, and outputs the amplified signal to the filter circuit 225. The amplifier circuit 224 amplifies an output signal of the contraction-relaxation signal extraction circuit 222, and outputs the amplified signal to the filter circuit 226. The amplification factor of the amplifier circuit 223 and the amplification factor of the amplifier circuit 224 are appropriately set. That is, it is preferable that the amplification factor of the amplifier circuit 223 be higher than the amplification factor of the amplifier circuit 224. Accordingly, the sensitivity of detecting a tremor signal by the detection module 30 is improved.

The filter circuit 225 extracts a frequency component of about 10 Hz, and attenuates a hum noise component and a DC component. Accordingly, a signal output from the filter circuit 225 becomes a tremor signal in accordance with a tremor, as illustrated in FIG. 8.

The amplitude of this tremor signal changes in accordance with the magnitude of the tremor. Specifically, the greater the tremor, the greater the amplitude of the tremor signal.

As illustrated in FIG. 8, a tremor signal is a signal with a certain frequency (e.g., about 10 Hz). The amplitude of a tremor signal changes in accordance with the state of load on the living body. Specifically, if there is almost no load being generated, such as when the living body is at rest, the amplitude of a tremor signal is very small, as illustrated in FIG. 8 (waveform on the left). In addition, if the living body is maintaining a posture and a load being generated is small (such as in the case where the living body is still and maintaining a posture against gravity), the amplitude of a tremor signal reaches a certain level (magnitude), as illustrated in FIG. 8 (waveform at the center). In addition, if the living body is maintaining a posture and a load being generated is great (such as in the case where the living body is successively maintaining a posture while being active), the amplitude of a tremor signal becomes yet greater, as illustrated in FIG. 8 (waveform on the right).

The filter circuit 226 extracts a frequency component lower than 10 Hz, which is more specifically an approximately DC component. Accordingly, a signal output from the filter circuit 226 becomes a component that is greatly displaced (component excluding a superimposed component) in FIG. 7, which becomes a contraction-relaxation signal in accordance with contraction and relaxation.

According to the exemplary aspect, the amplitude of this contraction-relaxation signal changes in accordance with the magnitude of the contraction and relaxation. Specifically, the greater the contraction and relaxation, the greater the amplitude of the contraction-relaxation signal.

Figure 9:
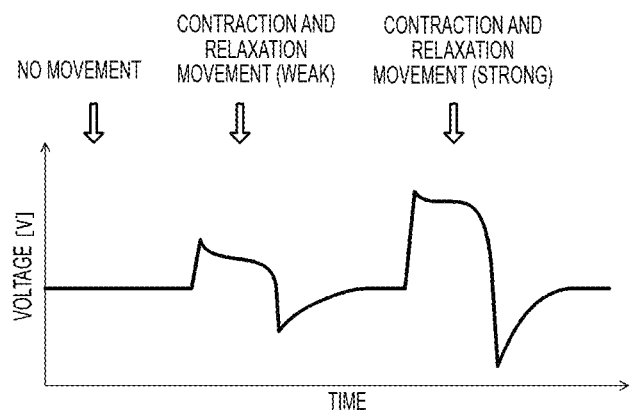
FIG. 9 is a waveform diagram illustrating an example of the waveform of a contraction-relaxation signal.

FIG. 9 is a waveform diagram illustrating an example of the waveform of a contraction-relaxation signal. As illustrated in FIG. 9, a contraction-relaxation signal is a signal responsive to the movement of the living body, and is, for example, an approximately DC component signal with a frequency lower than a tremor signal. The amplitude of a contraction-relaxation signal changes in accordance with the state of load on the living body. Specifically, when the living body is at rest and is not moving, the amplitude of a contraction-relaxation signal has an approximately reference voltage, as illustrated in FIG. 9 (waveform on the left). In addition, when the living body has a small movement that a tendon or a muscle contracts and relaxes (low load movement), the amplitude of a contraction-relaxation signal reaches a certain level (magnitude), as illustrated in FIG. 9 (waveform at the center). In addition, when the living body has a large movement that a tendon or a muscle contracts and relaxes (high load movement), the amplitude of a contraction-relaxation signal becomes yet greater, as illustrated in FIG. 9 (waveform on the right).

With the use of the signal processor 22 in this way, the sensor module 20 is configured to individually obtain and output a tremor signal and a contraction-relaxation signal from a voltage generated by the piezoelectric sensor 21. On this occasion, the sensor module 20 can extract and output a contraction-relaxation signal and a tremor signal with an amplitude in accordance with the state of load on a tendon or a muscle being observed.

(Configuration and Processing of Detection Module 30)

Figures 10, 11:
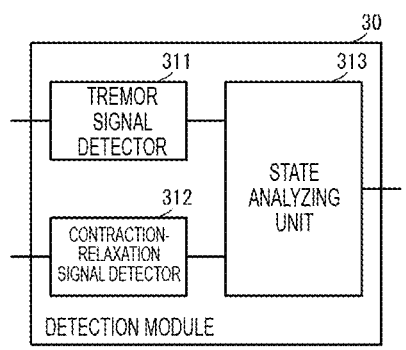
FIG. 10 is a block diagram illustrating the configuration of a detection module.
FIG. 11 is a diagram illustrating an example of an activity state analysis table.

FIG. 10 is a block diagram illustrating the configuration of the detection module. As illustrated in FIG. 10, the detection module 30 includes a tremor signal detector 311, a contraction-relaxation signal detector 312, and a state analyzing unit 313. Note that the detection module 30 only needs to include at least the tremor signal detector 311 and the contraction-relaxation signal detector 312. The detection module 30 can be realized by an MCU (or similar processing unit) or the like that is configured to execute software stored in memory for executing the algorithms disclosed herein.

A tremor signal is input from the signal processor 22 to the tremor signal detector 311. The tremor signal detector 311 detects the level (amplitude) of the tremor signal, and outputs the result to the state analyzing unit 313. A contraction-relaxation signal is input from the signal processor 22 to the contraction-relaxation signal detector 312. The contraction-relaxation signal detector 312 detects the level (amplitude) of the contraction-relaxation signal, and outputs the result to the state analyzing unit 313.

Using the level of the tremor signal and the level of the contraction-relaxation signal, the state analyzing unit 313 analyzes the activity state of a tendon or a muscle being observed. FIG. 11 is a diagram illustrating an example of an activity state analysis table.

(Case in which Isometric Contraction is Occurring, and No Isotonic Contraction is Occurring)

As illustrated in FIG. 11, when no isotonic contraction is occurring, and isometric contraction is occurring, the amplitude of the tremor signal becomes great, and the amplitude of the contraction-relaxation signal remains unchanged. Therefore, the state analyzing unit 313 determines that, if the average level of the amplitude of the tremor signal is greater than or equal to a threshold THa, and the average change amount of the amplitude of the contraction-relaxation signal is less than a threshold value THb (typically, the change amount remains substantially unchanged from a reference value), isometric contraction is occurring, and no isotonic contraction is occurring. Note that the state in which the average level of the amplitude of the tremor signal is greater than or equal to the threshold THa is the state in which there is a load in FIG. 8 (which corresponds to the waveform at the center in FIG. 8, and the waveform on the right in FIG. 8). In addition, the state in which the average change amount of the amplitude of the contraction-relaxation signal is less than the threshold THb or remains substantially unchanged from the reference value is the state in which there is no movement in FIG. 9 (which corresponds to the waveform on the left in FIG. 9).

(Case in which Isotonic Contraction is Occurring, and No Isometric Contraction is Occurring)

As illustrated in FIG. 11, when no isometric contraction is occurring, and isotonic contraction is occurring, the amplitude of the tremor signal becomes great, and the amplitude of the contraction-relaxation signal changes. Therefore, the state analyzing unit 313 determines that, if the average level of the amplitude of the tremor signal is greater than or equal to the threshold THa, and the average change amount of the amplitude of the contraction-relaxation signal is greater than or equal to the threshold THb, no isometric contraction is occurring, and isotonic contraction is occurring. Note that the state in which there is a change in the amplitude of the contraction-relaxation signal is the state in which there is a movement in FIG. 9 (which corresponds to the waveform at the center in FIG. 9 and the waveform on the right in FIG. 9).

(Case in which Passive Movement is Occurring)

A passive movement means that an external force is applied to a living body who has a tendon or a muscle being observed and the living body moves unintentionally. An exemplary passive movement is that, with the help of a therapist or care equipment during rehabilitation, a foot is moved by an external force.

As illustrated in FIG. 11, in the case where a passive movement is occurring, the amplitude of the tremor signal becomes small, and the amplitude of the contraction-relaxation signal changes. Therefore, the state analyzing unit 313 determines that, if the average level of the amplitude of the tremor signal is less than the threshold THa and the average change amount of the amplitude of the contraction-relaxation signal is greater than or equal to the threshold THb, a passive movement is occurring. Note that the state in which the average level of the amplitude of the tremor signal is less than the threshold THa is the state in which there is no load in FIG. 8 (which corresponds to the waveform on the left in FIG. 8).

(At Rest)

Being at rest means that a living body is not moving, and there is neither a load of maintaining a posture nor a passive movement.

As illustrated in FIG. 11, when the living body is at rest, the amplitude of the tremor signal becomes small, and the amplitude of the contraction-relaxation signal remains unchanged. Therefore, the state analyzing unit 313 determines that, if the average level of the amplitude of the tremor signal is less than the threshold THa and the average change amount of the amplitude of the contraction-relaxation signal is less than the threshold THb, the living body is at rest.

By using a signal from the sensor module 20 in this way, the detection module 30 individually detects the state in which only isometric contraction is occurring, the state in which isotonic contraction is occurring, the state in which a passive movement is occurring, and the state of being at rest.

In the above description, the mode in which the processing of the muscle activity observation apparatus 10 is realized by a plurality of functional units has been discussed. However, the mode in which a muscle activity observation method discussed as below is implemented as a program and stored in memory, and the program is read and executed by an arithmetic unit can be employed.

Figure 12:
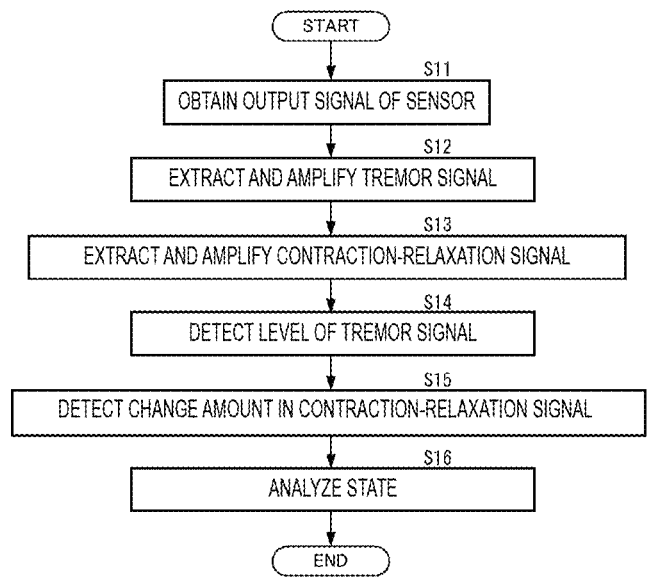
FIG. 12 is a flowchart of a muscle activity observation method.
Figure 13:
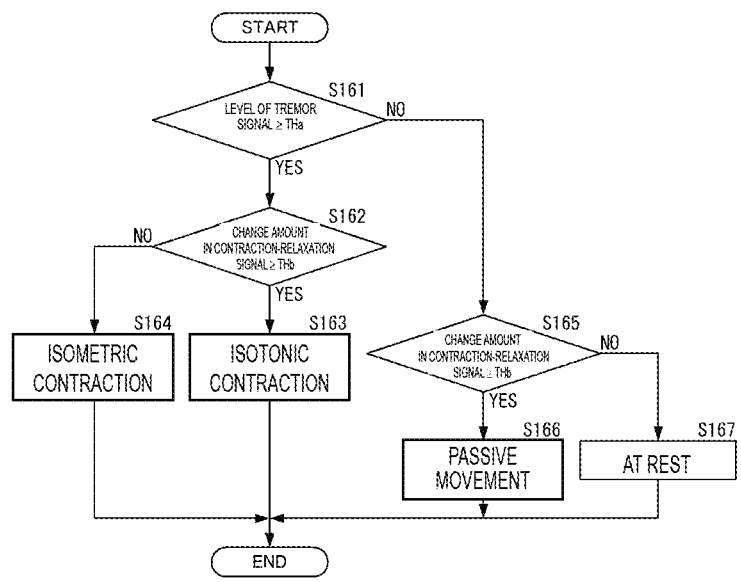
FIG. 13 is a flowchart of state analysis.

FIG. 12 is a flowchart of the muscle activity observation method. FIG. 13 is a flowchart of state analysis. It is noted that the specific contents of each process are described above, and descriptions thereof are omitted.

The arithmetic unit obtains an output signal of the sensor (S11). The arithmetic unit extracts a tremor signal from the output signal of the sensor, and amplifies the tremor signal (S12). The arithmetic unit extracts a contraction-relaxation signal from the output signal of the sensor, and amplifies the contraction-relaxation signal (S13). It is also noted that the order of the processing in step S12 and the processing in step S13 is not limited to this order. Instead, the order may be reversed, or the processing in step S12 and the processing in step S13 can be simultaneously performed in parallel.

The arithmetic unit detects the level of the tremor signal (S14). The arithmetic unit detects the change amount of the contraction-relaxation signal (S15). Again, it is noted that the order of the processing in step S14 and the processing in step S15 is not limited to this order. The order may be reversed, or the processing in step S14 and the processing in step S15 may be simultaneously performed in parallel.

Using the level of the tremor signal and the change amount of the contraction-relaxation signal, the arithmetic unit analyzes the activity state of a tendon or a muscle being observed (S16). Specifically, the arithmetic unit determines that, if the average level of the amplitude of the tremor signal is greater than or equal to the threshold THa (YES in S161) and the average change amount of the amplitude of the contraction-relaxation signal is greater than or equal to the threshold THb (YES in S162), isotonic contraction is occurring (S163). The arithmetic unit determines that, if the average level of the amplitude of the tremor signal is greater than or equal to the threshold THa (YES in S161) and the average change amount of the amplitude of the contraction-relaxation signal is less than the threshold THb (NO in S162), isometric contraction is occurring (S164). The arithmetic unit determines that, if the average level of the amplitude of the tremor signal is less than the threshold THa (NO in S161) and the average change amount of the amplitude of the contraction-relaxation signal is greater than or equal to the threshold THb (YES in S165), there is a passive movement (S166). The arithmetic unit determines that, if the average level of the amplitude of the tremor signal is less than the threshold THa (NO in S161) and the average change amount of the amplitude of the contraction-relaxation signal is less than the threshold THb (NO in S165), the living body is at rest (S167). For purposes of this disclosure, it is noted that "average" in the average level and the average change amount mentioned above is the average in a specified unit time.

In the above description, it is assumed that the frequency of tremors is about 10 Hz. However, the frequency of tremors may preferably be from 0.5 Hz to 100 Hz, and more preferably be from 3 Hz to 25 Hz, for example. This is because mechanical movements involved in involuntary movements include pathological tremors, mechanomyograms, microvibrations, and ballistocardiograms, in addition to physiological tremors. To make distinctions from these signals, it is preferable to configure a system that measures tremors with a frequency from 0.5 Hz to 100 Hz.

In addition, the center frequency of physiological tremors is from 8 Hz to 12 Hz; however, there are frequencies that depend on site. These frequencies are, for example, 3 Hz for the upper limbs, and 25 Hz for the fingers. Therefore, it is more preferable to configure a system that measures tremors with a frequency from 3 Hz to 25 Hz.

Figure 14:
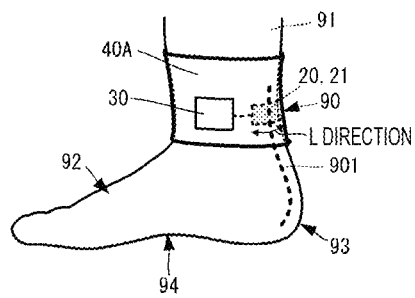
FIG. 14 is a side view illustrating the state in which the muscle activity observation apparatus is attached to a foot.

Although the above description has discussed the living body support 40 with a substantially L shape as viewed from the side by way of example, the living body support 40 can have a shape as illustrated in FIG. 14 in an alternative aspect. FIG. 14 is a side view illustrating the state in which the muscle activity observation apparatus is attached to a foot.

As illustrated in FIG. 14, a living body support 40A is cylindrical. The living body support 40A has a shape similar to the first portion 41 of the above-described living body support 40. The living body support 40A is arranged to cover the ankle 91.

In addition, in the configuration illustrated in FIG. 14, the sensor module 20 and the detection module 30 are arranged side by side along the circumferential direction of the cylinder of the living body support 40A, which is cylindrical. The sensor module 20 and the detection module 30 are connected by wiring that extends in this circumferential direction.

With the above configuration as illustrated in FIG. 14, for example, the configuration of the muscle activity observation apparatus 10 can be simplified, and the muscle activity observation apparatus 10 can be easily attached.

Figure 15A:
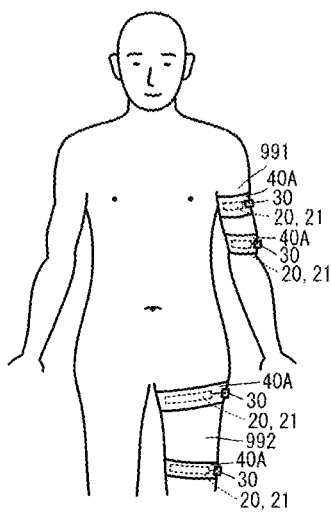
FIG. 15(A) and FIG. 15(B) are diagrams illustrating the mode in which the sensor module is attached to each of an arm (upper arm) and a thigh.
Figure 15B:
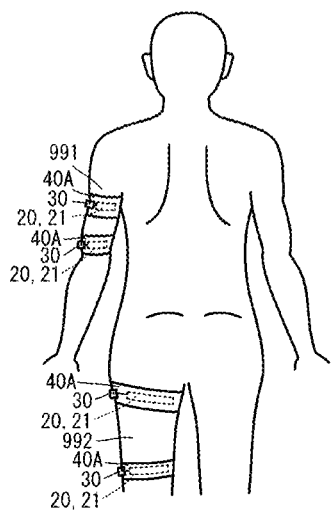
Figures 15C, 15D:
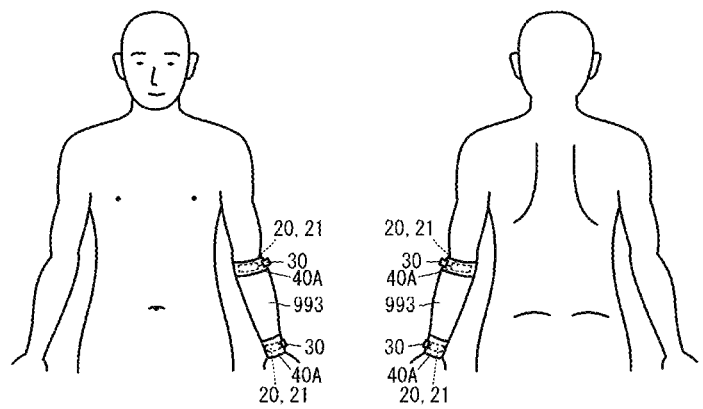
FIG. 15(C) and FIG. 15(D) are diagrams illustrating the mode in which the sensor module is attached to a forearm.
Figure 16A:
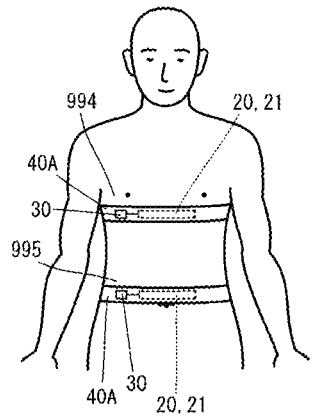
FIG. 16(A) and FIG. 16(B) are diagrams illustrating the mode in which the sensor module is attached to each of the chest, abdomen, upper back, and lower back.
Figure 16B:
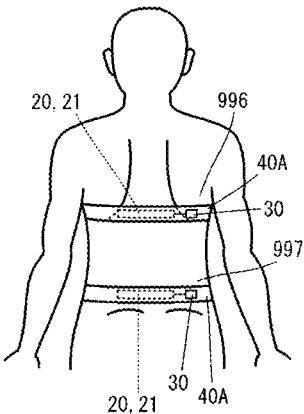

Although the sensor module 20 is attached to the foot in the above description, the sensor module 20 can also be attached to other sites of the body, as discussed below. FIG. 15(A) and FIG. 15(B) illustrate the mode in which the sensor module 20 is attached to each of an arm (upper arm) and a thigh, and FIG. 15(C) and FIG. 15(D) illustrate the mode in which the sensor module 20 is attached to a forearm. FIG. 16(A) and FIG. 16(B) are diagrams illustrating the mode in which the sensor module 20 is attached to each of the chest, abdomen, upper back, and lower back.

As illustrated in FIG. 15(A) and FIG. 15(B), when the sensor module 20 is attached to an upper arm 991, it is preferable to make the length direction of the piezoelectric sensor 21 of the sensor module 20 be orthogonal to a direction in which the upper arm 991 extends. In addition, as illustrated in FIG. 15(A) and FIG. 15(B), when the sensor module 20 is attached to a thigh 992, it is preferable to make the length direction of the piezoelectric sensor 21 of the sensor module 20 be orthogonal to a direction in which the thigh 992 extends. In addition, as illustrated in FIG. 15(C) and FIG. 15(D), when the sensor module 20 is attached to a forearm 993, it is preferable to make the length direction of the piezoelectric sensor 21 of the sensor module 20 be orthogonal to a direction in which the forearm 993 extends. Although two pairs of the sensor module 20 and the detection module 30 are attached to each attachment target in FIG. 15(A) and FIG. 15(B), only one pair may be attached.

In addition, as illustrated in FIG. 16(A) and FIG. 16(B), when the sensor module 20 is attached to each of a chest 994 and an upper back 996, it is preferable to make the length direction of the piezoelectric sensor 21 of the sensor module 20 be parallel to the width direction of the chest 994 and the upper back 996. In addition, as illustrated in FIG. 16(A) and FIG. 16(B), when the sensor module 20 is attached to each of an abdomen 995 and a lower back 997, it is preferable to make the length direction of the piezoelectric sensor 21 of the sensor module 20 be parallel to the width direction of the abdomen 995 and the lower back 997.

With regard to the attachment modes in FIG. 15(A), FIG. 15(B), FIG. 15(C), FIG. 15(D), FIG. 16(A), and FIG. 16(B), for example, the sensor modules 20 on the front and back of the body may be arranged in one living body support 40A, and one common detection module 30 arranged similarly in the living body support 40A may be connected to these sensor modules 20.

By having the foot as a target being detected, a tremor signal and the like may be detected using a sock itself, or a tremor signal and the like may be detected on top of a sock or a stocking. In addition, muscle load and ankle joint movement may be detected at the same time. The legs or the feet are attachment positions far from human consciousness so that the person wearing the sensor module 20 may easily forget that he/she is wearing the sensor module 20, and, as compared to the arms, lower back, chest, and the like, the person may feel less uncomfortable toward wearing the sensor module 20. If the sensor module 20 is attached around the minimum leg girth, the attachment is not affected by whether there is a shoe or a sock. Muscles important for activities of daily living, maintaining a posture, and walking, such as the tibialis anterior muscle, the soleus muscle, and peroneus longus muscle and the gastrocnemius muscle, may be detected and observed. If the sensor modules 20 are attached to both legs, the sensor modules 20 may be used for analysis and quantification of walking, jogging, lower limb training, lower limb rehabilitation, and the like.

Second Exemplary Embodiment

Figure 17:
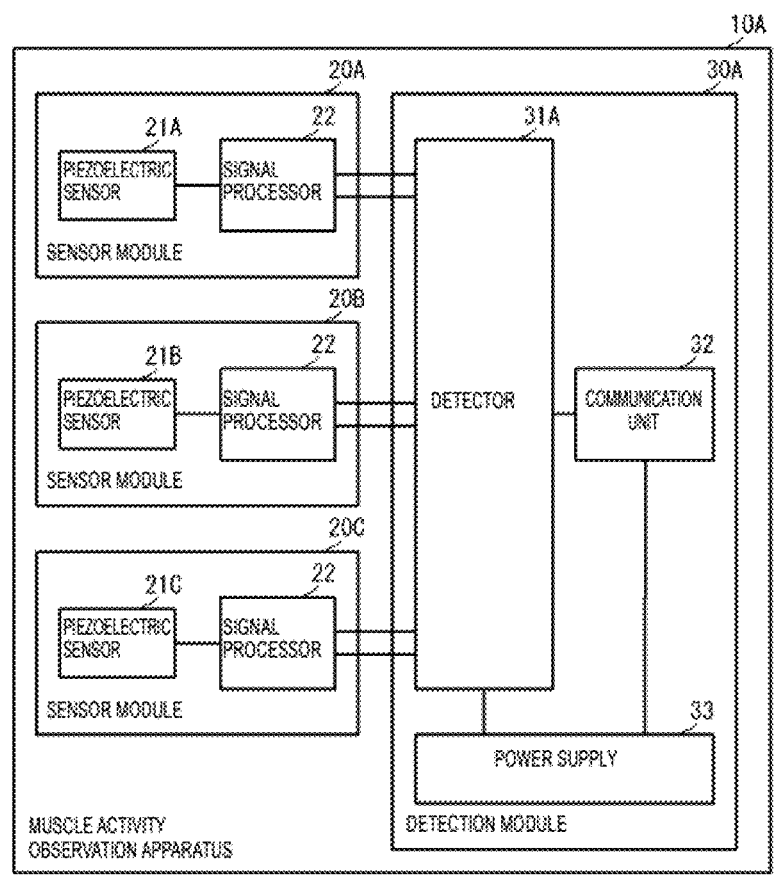
FIG. 17 is a block diagram illustrating the configuration of a muscle activity observation apparatus according to a second exemplary embodiment.

A muscle activity observation apparatus according to a second exemplary embodiment will be described with reference to the drawings. FIG. 17 is a block diagram illustrating the configuration of the muscle activity observation apparatus according to the second embodiment. FIG. 18(A) is a side view illustrating the state in which the muscle activity observation apparatus is attached to a foot, and FIG. 18(B) is a plan view illustrating the state in which the muscle activity observation apparatus is attached to the foot.

As illustrated in FIG. 17, a muscle activity observation apparatus 10A according to the second embodiment is different from the muscle activity observation apparatus 10 according to the first embodiment in the point that the muscle activity observation apparatus 10A includes a sensor module 20A, a sensor module 20B, and a sensor module 20C, and in the processing performed by a detector 31A. The rest of the configuration of the muscle activity observation apparatus 10A is the same as the muscle activity observation apparatus 10, and descriptions of the same portions are omitted.

According to the exemplary aspect, the sensor module 20A, the sensor module 20B, and the sensor module 20C have the same configuration and execute the same processing as the sensor module 20 according to the first embodiment. As illustrated in FIG. 18(A) and FIG. 18(B), a piezoelectric sensor 21A of the sensor module 20A is attached to the minimum leg girth 90 so as to overlap the Achilles tendon 901. A piezoelectric sensor 21B of the sensor module 20B is attached to overlap the tibialis anterior muscle tendon 902. A piezoelectric sensor 21C of the sensor module 20C is attached to overlap the peroneus longus muscle tendon 903. That is, it is assumed that the muscle activity observation apparatus 10A has plural points for detecting tendon or muscle activities.

The sensor module 20A, the sensor module 20B, and the sensor module 20C output tremor signals and contraction-relaxation signals, which are respectively extracted by the sensor modules 20A, 20B, and 20C, to the detector 31A of a detection module 30A.

Like the above-described detector 31, the detector 31A detects isometric contraction, isotonic contraction, a passive movement, or being at rest, and analyzes the movement state of the foot. FIG. 19 is a table illustrating an example of the relationship among a site, a movement, and a tendon or a muscle being observed.

If the detector 31A detects isotonic contraction from the tremor signal and the contraction-relaxation signal of the sensor module 20A, the detector 31A detects contraction and relaxation of the Achilles tendon 901 or the soleus muscle or the gastrocnemius muscle. That is, by detecting the activity of the Achilles tendon, the detector 31A can detect the activities of soleus muscle and/or the gastrocnemius muscle since the Achilles tendon 901 connects the soleus muscle to a bone, also connects the gastrocnemius muscle to a bone. Similarly, if the detector 31A detects isotonic contraction from the tremor signal and the contraction-relaxation signal of the sensor module 20B, the detector 31A detects contraction and relaxation of the tibialis anterior muscle tendon 902 or the tibialis anterior muscle. If the detector 31A detects isotonic contraction from the tremor signal and the contraction-relaxation signal of the sensor module 20C, the detector 31A can thus also detect contraction and relaxation of the peroneus longus muscle tendon 903 or the peroneus longus muscle.

Using contraction and relaxation of the Achilles tendon 901, contraction and relaxation of the tibialis anterior muscle tendon 902, and contraction and relaxation of the peroneus longus muscle tendon 903, the detector 31A detects the movement state of the foot (e.g., the lower leg). For example, as illustrated in FIG. 19, if the detector 31A detects contraction and relaxation of the Achilles tendon 901 (or contraction and relaxation of the soleus muscle, the gastrocnemius muscle, and the like), the detector 31A determines that there is flexion (e.g., plantar flexion) or inversion of the foot. In addition, as illustrated in FIG. 19, if the detector 31A detects contraction and relaxation of the tibialis anterior muscle tendon 902 (or contraction and relaxation of the tibialis anterior muscle), the detector 31A determines that there is extension (dorsiflexion) of the foot. In addition, as illustrated in FIG. 19, if the detector 31A detects contraction and relaxation of the peroneus longus muscle tendon 903 (or contraction and relaxation of the peroneus longus muscle), the detector 31A determines that there is eversion of the foot. In this way, the muscle activity observation apparatus 10A may determine various movement states of the foot.

Thus, in an exemplary aspect, the muscle activity observation apparatus 10A can include the sensor module 20A and the sensor module 20B to detect an activity state of at least one of an Achilles tendon, a soleus muscle and a gastrocnemius muscle. Alternatively or in addition thereto, the muscle activity observation apparatus 10A can include the sensor module 20A and the sensor module 20C to detect an activity state of at least one of a tibialis anterior muscle tendon, tibialis anterior muscle, a peroneus longus muscle tendon and a peroneus longus muscle.

Besides the foot, by realizing attachment modes as illustrated in FIG. 15(A), FIG. 15(B), FIG. 15(C), FIG. 15(D), FIG. 16(A), and FIG. 16(B) described above, the movement state is detected for other sites, as illustrated in FIG. 19.

For example, by detecting contraction and relaxation of the quadriceps femoris muscle, flexion of the knee (thigh) may be determined. By detecting contraction and relaxation of hamstrings, extension of the knee (thigh) may be determined. By detecting contraction and relaxation of the palmar flexor muscles (flexor digitorum *profundus*, flexor digitorum superficialis, flexor pollicis longus, etc.), flexion (palm flexion) of the hand and fingers may be determined. By detecting contraction and relaxation of the palmar dorsiflexor muscles (extensor digitorum, etc.), extension (dorsiflexion) of the hand and fingers may be determined. By detecting contraction and relaxation of the biceps, flexion of the elbow (upper arm) may be determined. By detecting contraction and relaxation of the triceps, extension of the elbow (upper arm) may be determined. By detecting contraction and relaxation of the rectus abdominis muscle, flexion of the abdomen and lower back (spinal anteflexion) may be determined. By detecting contraction and relaxation of the intrinsic back muscles (erector spinae muscles, etc.), extension of the abdomen and lower back (spinal retroflexion) may be determined. By detecting contraction and relaxation of the pectoralis major, flexion (contraction) of the chest may be determined. By detecting contraction and relaxation of the latissimus dorsi, extension of the chest may be determined.

Third Exemplary Embodiment

Figure 20A:
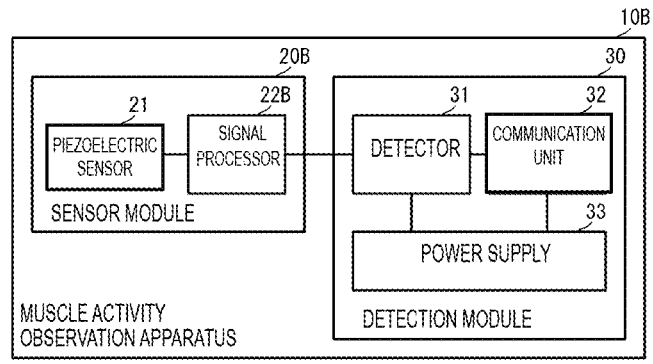
FIG. 20(A) is a block diagram illustrating the configuration of a muscle activity observation apparatus according to a third exemplary embodiment.
Figure 20B:
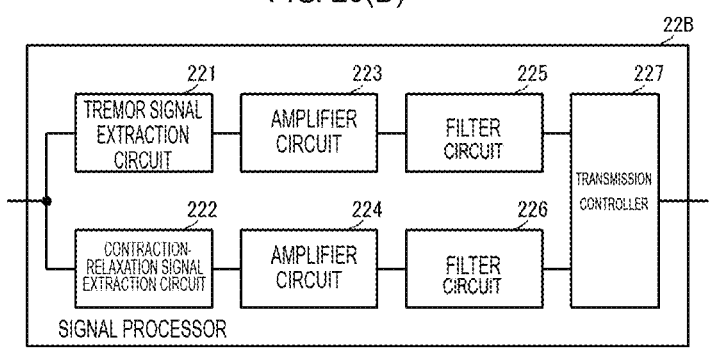
FIG. 20(B) is a block diagram illustrating the configuration of a signal processor.

A muscle activity observation apparatus according to a third exemplary embodiment will be described with reference to the drawings. FIG. 20(A) is a block diagram illustrating the configuration of the muscle activity observation apparatus according to the third embodiment. FIG. 20(B) is a block diagram illustrating the configuration of a signal processor.

As illustrated in FIG. 20(A), a muscle activity observation apparatus 10B according to the third embodiment is different from the muscle activity observation apparatus 10 according to the first embodiment in the point that the muscle activity observation apparatus 10B includes a signal processor 22B and a sensor module 20B. It is noted that the rest of the configuration of the muscle activity observation apparatus 10B is the same as the muscle activity observation apparatus 10, and descriptions of the same portions are omitted.

The signal processor 22B further includes a transmission controller 227 in addition to the elements of the signal processor 22. The transmission controller 227 is connected to the filter circuit 225 and the filter circuit 226. The transmission controller 227 transmits a tremor signal and a contraction-relaxation signal in time division to the detector 31.

With such a configuration, the configuration of a communication cable that connects the sensor module 20B and the detection module 30 may be simplified.

Fourth Exemplary Embodiment

Figure 21:
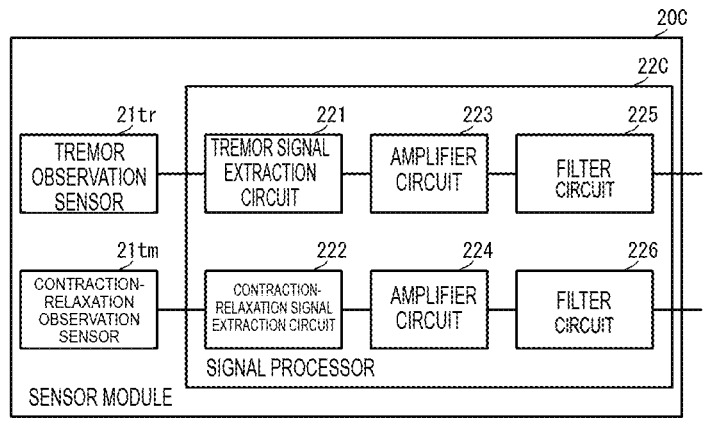
FIG. 21 is a block diagram illustrating the configuration of a sensor module of a muscle activity observation apparatus according to a fourth exemplary embodiment.

A muscle activity observation apparatus according to a fourth exemplary embodiment will be described with reference to the drawings. FIG. 21 is a block diagram illustrating the configuration of a sensor module of the muscle activity observation apparatus according to the fourth embodiment.

As illustrated in FIG. 21, a sensor module 20C is different from the sensor module 20 in the point that the sensor module 20C does not include the piezoelectric sensor 21, but includes a tremor observation sensor 21*tr* and a contraction-relaxation observation sensor 21*tm*. The rest of the configuration of the sensor module 20C is the same as the sensor module 20, and descriptions of the same portions are omitted.

The tremor observation sensor 21*tr* is a sensor that detects the above-described tremor signal. For example, the tremor observation sensor 21*tr* is realized by an acceleration sensor, a microphone, or the like. Note that the tremor observation sensor 21*tr* may also be realized by the piezoelectric sensor 21. In addition, the tremor observation sensor 21*tr* may be other sensors as long as they are capable of detecting a signal of about 10 Hz.

The tremor observation sensor 21*tr* outputs an electric change based on a tremor to the tremor signal extraction circuit 221 of a signal processor 22C.

The contraction-relaxation observation sensor 21*tm* is a sensor that detects the above-described contraction-relaxation signal. For example, the contraction-relaxation observation sensor 21*tm* is realized by the piezoelectric sensor 21. It is noted that the contraction-relaxation observation sensor 21*tm* can be other sensors as long as their states change in accordance with contraction and relaxation of a tendon or a muscle being observed, and they are capable of obtaining an electric signal in accordance with this change in state. As other sensors, for example, a pressure sensor using a pressure-sensitive film, or a pressure sensor/load sensor that detects a strain change or a change in electrostatic capacitance due to diaphragm deformation may be used.

The contraction-relaxation observation sensor 21*tm* outputs an electric change based on contraction and relaxation of a tendon or a muscle to the contraction-relaxation signal extraction circuit 222 of the signal processor 22C.

Like the sensor module 20C, a sensor that is configured to detect a tremor signal and a sensor that is configured to detect a contraction-relaxation signal may be separately provided. In that case, the auxiliary plate of a sensor that detects a tremor signal and the auxiliary plate of a sensor that detects a contraction-relaxation signal may be made of a material and have characteristics that are suitable for detecting the respective signals.

Fifth Exemplary Embodiment

Figure 22:
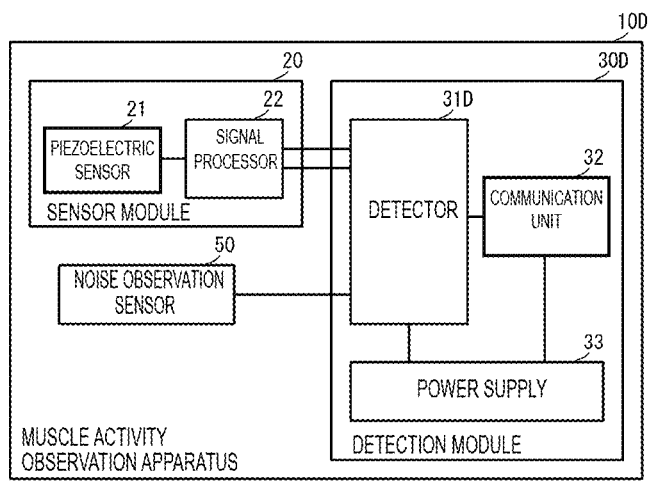
FIG. 22 is a block diagram illustrating the configuration of a sensor module of a muscle activity observation apparatus according to a fifth exemplary embodiment.

A muscle activity observation apparatus according to a fifth exemplary embodiment will be described with reference to the drawings. FIG. 22 is a block diagram illustrating the configuration of a sensor module of the muscle activity observation apparatus according to the fifth embodiment.

As illustrated in FIG. 22, a muscle activity observation apparatus 10D according to the fifth embodiment is different from the muscle activity observation apparatus 10 according to the first embodiment in the point that a noise observation sensor 50 is added, and in the processing performed by a detector 31D. The rest of the configuration of the muscle activity observation apparatus 10D is the same as the muscle activity observation apparatus 10, and descriptions of the same portions are omitted.

In an exemplary aspect, the noise observation sensor 50 is, for example, an acceleration sensor, and detects the movement of a site of a living body being observed and generates movement noise. Moreover, the noise observation sensor 50 is configured to output the movement noise to the detector 31D.

Using the movement noise, the detector 31D suppresses noise included in a tremor signal and a contraction-relaxation signal.

With this configuration, the detector 31D more accurately analyzes the movement state of a tendon or a muscle.

In the configuration of each of the exemplary embodiments, detection of a tremor signal can be used for activating the muscle activity observation apparatus. For example, the muscle activity observation apparatus only observes the level of a tremor signal in sleep mode. Upon detection that the average level of the amplitude of a tremor signal becomes greater than or equal to the threshold THa, the muscle activity observation apparatus is activated from sleep mode, and observes a tremor signal and a contraction-relaxation signal. In this way, the power of the muscle activity observation apparatus may be saved.

In addition, the piezoelectric sensor is attached using the living body support 40 in each of the embodiments. However, the piezoelectric sensor may be directly attached to the living body without using the living body support 40.

In addition, the piezoelectric sensor is arranged over a specific tendon near the ankle in the above description. However, the position where the piezoelectric sensor is arranged is not limited to this, and the position only needs to overlap a tendon or a muscle being observed. Furthermore, the position need not overlap the tendon or the muscle, as long as the position is affected by the movement of the tendon or the muscle.

In addition, the mode in which polylactic acid or aluminum nitride is used for the material of the piezoelectric body of the piezoelectric sensor has been discussed in the above description. However, for the material of the piezoelectric body, a thin film made of the following inorganic piezoelectric materials may be used: crystal; PZT and (Pb, La) (Zr, Ti) OX perovskite compound (PZLT), which are piezoelectric ceramics; and lead zirconate niobate-lead titanate solid solution (PZN-PT), lead magnesium niobate-lead titanate solid solution (PMN-PT), lithium niobate ($LiNbO_3$), lithium tantalate ($LiTaO_3$), potassium niobate ($KNbO_3$), and zinc oxide (ZnO), which are piezoelectric single crystals. In addition, the following organic piezoelectric materials may also be used: polyvinylidene fluoride, polyvinylidene fluoride copolymer, polyvinylidene cyanide, vinylidene cyanide copolymer, odd nylon such as nylon 9 and nylon 11, aromatic nylon, alicyclic nylon, polyhydroxycarboxylic acid such as polyhydroxybutyrate, cellulose derivative, and polyurea.

In addition, although the living body support 40 is tubular in the above described exemplary embodiments, the living body support 40 may be strip-shaped or may be clothing such as a sock according to alternative aspects.

Moreover, Configurations of the muscle activity observation apparatuses discussed in the above-described embodiments can be combined as appropriate, and operational effects corresponding to each combination may be obtained.

In the above description, the state of a tendon or a muscle being observed is analyzed using a tremor and contraction-relaxation. However, the analysis may be conducted only with a tremor. When using only a tremor, the configuration of the apparatus may be simplified in quantification that does not require the analysis of muscle contraction (bending). The apparatus may be located not only at a position where there is a tendon, but also at a position where there is the belly of a muscle, for example, thereby increasing the degree of freedom in locating the apparatus. Instead of a piezoelectric film as described above, an acceleration sensor or a microphone (highly sensitive microphone) may be used.

(Exemplary Configuration of Muscle Activity Observation System)

Figure 23:
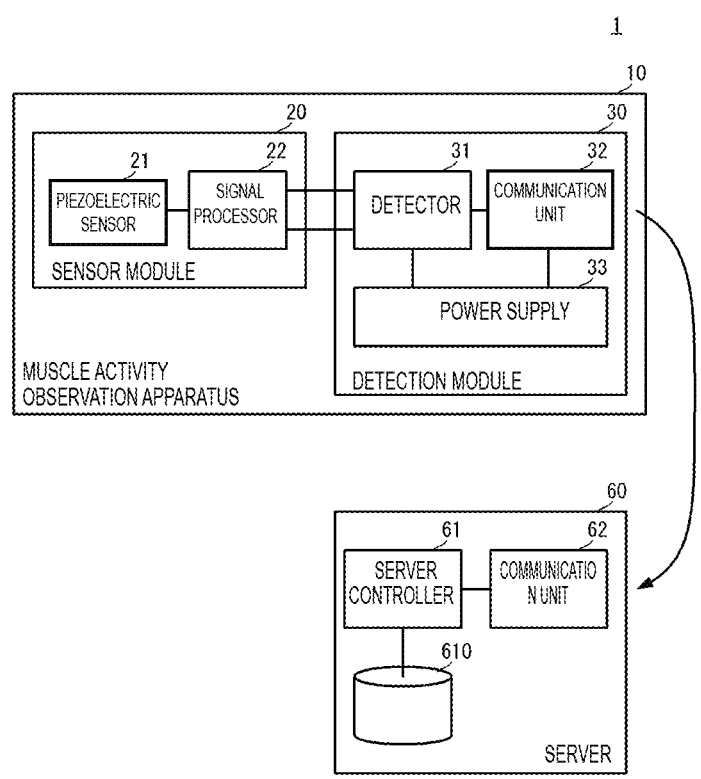
FIG. 23 is a block diagram illustrating an exemplary first mode of a muscle activity observation system.
Figure 24:
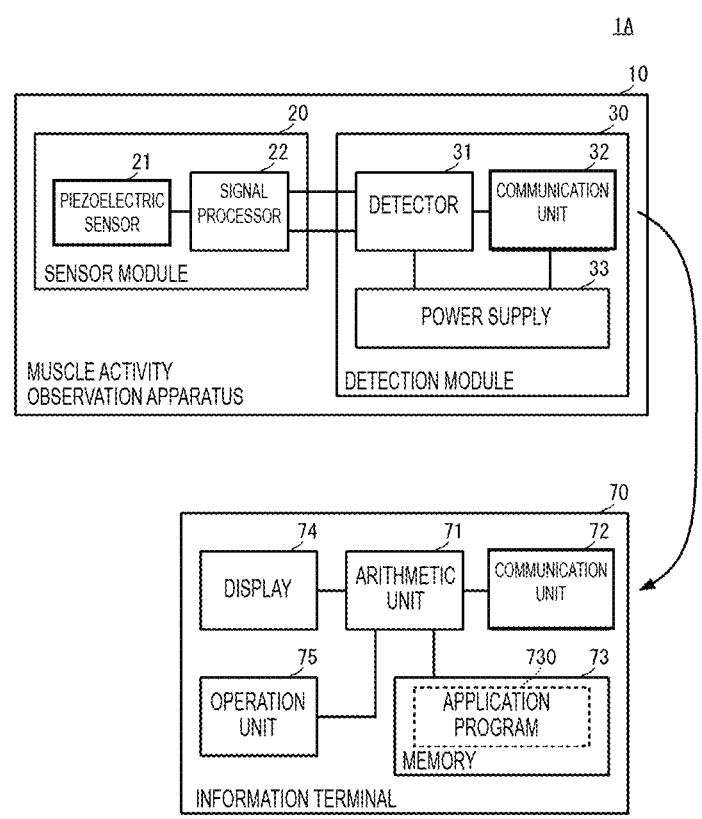
FIG. 24 is a block diagram illustrating an exemplary second mode of the muscle activity observation system.

The muscle activity observation apparatus discussed in each of the above-described embodiments can be adopted in, for example, a muscle activity observation system as illustrated in FIG. 23 and FIG. 24. Although the mode in which the muscle activity observation apparatus 10 according to the first embodiment is used will be discussed in the following description, the muscle activity observation apparatuses according to other embodiments may also be used.

FIG. 23 is a block diagram illustrating an exemplary first mode of the muscle activity observation system. As illustrated in FIG. 23, a muscle activity observation system 1 includes the muscle activity observation apparatus 10 and a server 60.

The server 60 includes, for example, a server controller 61, a communication unit 62, and a database 610. The server controller 61 controls the entire server 60. In addition, the server controller 61 registers and reads the analysis result of a tendon or muscle activity, the movement state of a foot, and so forth in and from the database 610.

The communication unit 62 performs data communication with the communication unit 32 of the muscle activity observation apparatus 10. The communication unit 62 receives the analysis result of a tendon or muscle activity, the movement state of a foot, and the like from the muscle activity observation apparatus 10, and outputs the received data to the server controller 61. Communication between the communication unit 62 and the communication unit 32 may be wireless communication or wired communication.

With the above-described configuration, the analysis result of a tendon or muscle activity, the movement state of a foot, and the like, which are obtained by the muscle activity observation apparatus 10, are stored in the database, and the user may use these items of data as needed.

FIG. 24 is a block diagram illustrating an exemplary second mode of the muscle activity observation system. As illustrated in FIG. 24, a muscle activity observation system 1A includes the muscle activity observation apparatus 10 and an information terminal 70.

The information terminal 70 includes, for example, an arithmetic unit 71, a communication unit 72, a memory 73, a display 74, and an operation unit 75.

The arithmetic unit 71 is configured to control the entire information terminal 70. The communication unit 72 performs data communication with the communication unit 32 of the muscle activity observation apparatus 10. Communication between the communication unit 72 and the communication unit 32 may be wireless communication or wired communication. The communication unit 72 receives the analysis result of a tendon or muscle activity, the movement state of a foot, and the like from the muscle activity observation apparatus 10, and outputs the received data to the arithmetic unit 71. The memory 73 stores an application program 730. In addition, the memory 73 stores the analysis result of a tendon or muscle activity, the movement state of a foot, and the like, which are received using the communication unit 72. The display 74 includes a liquid crystal display or the like. The operation unit 75 includes a touchscreen or the like.

The arithmetic unit 71 is configured to read and execute the application program 730 from the memory 73 in accordance with an operation input or the like from the operation unit 75. The application program 730 is, for example, a program for visualizing the analysis result of a tendon or muscle activity, the movement state of a foot, and the like.

Moreover, the arithmetic unit 71 is configured to execute the application program 730. On this occasion, the arithmetic unit 71 executes the application program 730 using the analysis result of a tendon or muscle activity, the movement state of a foot, and the like, which are received by the communication unit 72 or stored in the memory 73. The arithmetic unit 71 displays the result of executing the application program 730 on the display 74.

With the above-described configuration, while observing the analysis result of a tendon or muscle activity, the movement state of a foot, and the like using the muscle activity observation apparatus 10, the user may visually and easily recognize the observation result.

Configurations of the above-described muscle activity observation systems may be combined as appropriate, and operational effects corresponding to each combination may be obtained.

REFERENCE SIGNS LIST 1, 1A: muscle activity observation system
10, 10A, 10B, 10D: muscle activity observation apparatus
20, 20A, 20B, 20C: sensor module
21, 21A, 21B, 21C: piezoelectric sensor
21tm: contraction-relaxation observation sensor
21tr: tremor observation sensor
22, 22B, 22C: signal processor
22M: signal processing circuit module
30, 30A: detection module
31, 31A, 31D: detector
32: communication unit
33: power supply
40, 40A: living body support
41: first portion
42: second portion
43: hole
50: noise observation sensor
60: server
61: server controller
62: communication unit
70: information terminal
71: arithmetic unit
72: communication unit
73: memory
74: display
75: operation unit
121: tremor signal extraction circuit
201: piezoelectric body
202: detection electrode
203: adhesion layer
204: auxiliary plate
220C: transmission cable
220M: connection terminal
221: tremor signal extraction circuit
222: contraction-relaxation signal extraction circuit
223, 224: amplifier circuit 225, 226: filter circuit
227: transmission controller
311: tremor signal detector
312: contraction-relaxation signal detector
313: state analyzing unit
610: database
730: application program
90: minimum leg girth
91: ankle
92: instep
93: heel
94: sole
901: Achilles tendon
902: tibialis anterior muscle tendon
903: peroneus longus muscle tendon
991: upper arm
992: thigh
993: forearm
994: chest
995: abdomen
996: upper back
997: lower back

The invention claimed is:

1. A muscle activity detection apparatus comprising:
a first sensor configured to generate an output signal that changes based on a tremor of a tendon or a muscle;
a second sensor configured to generate an output signal that changes based on contraction and relaxation of the tendon or the muscle;
a state analyzing unit configured to determine: (1) whether an average level of an amplitude of the output signal of the first sensor is greater than or equal to a first threshold, and (2) whether an average change amount of the output signal of the second sensor is less than a second threshold value; and
a detector configured to detect whether the tendon or the muscle is a state where isotonic contraction is occurring or a state where isometric contraction is occurring based on the respective output signals of the first sensor and the second sensor,
wherein at least one of the first sensor and the second sensor comprises a flat-film shaped piezoelectric sensor that is arranged side by side with a thin signal processing circuit module, and
wherein a connection terminal is disposed on a side of the thin signal processing circuit module that is opposite to the flat-film shaped piezoelectric sensor and is coupled to the detector.

2. The muscle activity detection apparatus according to claim 1, wherein
the detector is further configured to detect whether the tendon or the muscle is in a state of rest.

3. The muscle activity detection apparatus according to claim 1, wherein the flat-film shaped piezoelectric sensor is a single sensor comprises both the first sensor and the second sensor.

4. The muscle activity detection apparatus according to claim 3, wherein the flat-film shaped piezoelectric sensor comprises a rectangle shaped main surface and is sheet-shaped.

5. The muscle activity detection apparatus according to claim 4, wherein the flat-film shaped piezoelectric sensor includes an auxiliary plate disposed in parallel to the main surface, with the auxiliary plate having a hardness greater than a hardness of a piezoelectric body included in the flat-film shaped piezoelectric sensor.

6. The muscle activity detection apparatus according to claim 4, wherein the main surface having the rectangle shape has a length direction that is substantially orthogonal to a direction of the tendon or the muscle when the muscle activity detection apparatus is attached to a living body having the tendon or the muscle.

7. The muscle activity detection apparatus according to claim 1,
wherein the first sensor and the second sensor comprise at least one of a plurality of combinations of sensors, and
wherein the detector is configured to detect the state of the tendon or the muscle based on the respective output signals of the first sensor and the second sensor of the plurality of combinations.

8. The muscle activity detection apparatus according to claim 1, wherein the detector is configured to detect a movement of a site of a living body having the tendon or the muscle from the detected state of the tendon or the muscle.

9. The muscle activity detection apparatus according to claim 1, further comprising:
a living body support shaped to fit an outer shape of a living body that includes the tendon or the muscle,
wherein the first sensor and the second sensor are attached to the living body support.

10. The muscle activity detection apparatus according to claim 1, further comprising:
a signal processor configured to extract a tremor signal from the output signal generated by the first sensor, extract a contraction-relaxation signal from the output signal generated by the second sensor, amplify the tremor signal and the contraction-relaxation signal, and output the amplified signals to the detector,
wherein the detector is further configured to detect the state of the tendon or the muscle using the tremor signal and the contraction-relaxation signal.

11. The muscle activity detection apparatus according to claim 10, wherein the signal processor is configured to output the tremor signal and the contraction-relaxation signal in time division.

12. The muscle activity detection apparatus according to claim 1, further comprising a communication unit configured to communicate a detection result obtained by the detector.

13. A muscle activity detection system comprising:
the muscle activity detection apparatus according to claim 1; and
a server configured to store, in a database, an analysis result of an activity of the tendon or the muscle, with the analysis result being determined from the respective output signals of the first sensor and the second sensor.

14. The muscle activity detection apparatus according to claim 1, wherein the detector is further configured to detect that the tendon or the muscle is the state that isometric contraction is occurring and isotonic contraction is not occurring when the average level of the amplitude of the output signal of the first sensor is greater than or equal to the first threshold and the average change amount of the output signal of the second sensor is less than the second threshold value.

15. The muscle activity detection apparatus according to claim 1, wherein the detector is further configured to detect that there is no movement of the tendon or the muscle when the average change amount of the output signal of the second sensor is less than the second threshold value.

16. The muscle activity detection apparatus according to claim 1, wherein the detector is further configured to detect that the tendon or the muscle is the state that isotonic contraction is occurring and isometric contraction is not occurring when the average level of the amplitude of the output signal of the first sensor is greater than or equal to the first threshold and the average change amount of the output signal of the second sensor is greater than or equal to the second threshold value.

17. A muscle activity detection method comprising:
detecting, by at least one sensor, a tremor of a tendon or a muscle and generating a tremor signal in response to the detecting of the tremor;
detecting, by the at least one sensor, contraction and relaxation of the tendon or the muscle and generating a contraction-relaxation signal in response to the detecting of the contraction and relaxation;
determining whether an average level of an amplitude of the tremor signal generated by the at least one sensor is greater than or equal to a first threshold;
determining whether an average change amount of the contraction-relaxation signal generated by the at least one sensor is less than a second threshold value; and
detecting whether the tendon or the muscle is a state where isotonic contraction is occurring or a state where isometric contraction is occurring based on the tremor signal and the contraction-relaxation signal,
wherein the at least one sensor comprises a flat-film shaped piezoelectric sensor that is arranged side by side with a thin signal processing circuit module, and a connection terminal is disposed on a side of the thin signal processing circuit module that is opposite to the flat-film shaped piezoelectric sensor and is coupled to the detector.

18. The muscle activity detection method according to claim 17, further comprising detecting, using the tremor signal and the contraction-relaxation signal, whether the tendon or the muscle is in a rest state.

19. The muscle activity detection method according to claim 17, further comprising detecting the tremor signal and the contraction-relaxation signal with a single sensor that comprises the at least one sensor.

20. The muscle activity detection method according to claim 19, wherein the single sensor is the flat-film shaped piezoelectric sensor.

21. The muscle activity detection method according to claim 19, further comprising arranging the single sensor so that a direction with high detection sensitivity is substantially orthogonal to a direction in which the tendon or the muscle extends.

22. The muscle activity detection method according to claim 17, further comprising detecting the state of the tendon or the muscle using the tremor signal and the contraction-relaxation signal detected at a plurality of points.

23. The muscle activity detection method according to claim 17, further comprising detecting a movement of a site of a living body including the tendon or the muscle from the state of the tendon or the muscle.

24. The muscle activity detection method according to claim 17, further comprising amplifying the tremor signal and the contraction-relaxation signal and detecting the state of the tendon or the muscle based on the amplified signals.

25. The muscle activity detection method according to claim 17, further comprising outputting the tremor signal and the contraction-relaxation signal in time division.

26. The muscle activity detection method according to claim 17, further comprising communicating a result of detecting the tendon or the muscle that obtained from the tremor signal and the contraction-relaxation signal.

27. The muscle activity detection method according to claim 17, further comprising detecting that the tendon or the muscle is the state that isometric contraction is occurring and isotonic contraction is not occurring when the average level of the amplitude of the tremor signal generated by the at least one sensor is greater than or equal to the first threshold and the average change amount of the contraction-relaxation signal generated by the at least one sensor is less than the second threshold value.

28. The muscle activity detection method according to claim 17, further comprising detecting that there is no movement of the tendon or the muscle when the average change amount of the contraction-relaxation signal generated by the at least one sensor is less than the second threshold value.

29. The muscle activity detection method according to claim 17, further comprising detecting that the tendon or the muscle is the state that isotonic contraction is occurring and isometric contraction is not occurring when the average level of the amplitude of the tremor signal generated by the at least one sensor is greater than or equal to the first threshold and the average change amount of the contraction-relaxation signal generated by the at least one sensor is greater than or equal to the second threshold value.

30. A muscle activity detection apparatus comprising:
a sensor module comprising a flat-film shaped piezoelectric sensor that is configured to generate an output signal that changes based on a tremor of a tendon or a muscle, and further configured to generate an output signal that changes based on contraction and relaxation of the tendon or the muscle;
a thin signal processing circuit module that is arranged side by side the sensor module and is configured to extract a tremor signal from the output signal generated by the sensor module, extract a contraction-relaxation signal from the output signal generated by the sensor module, amplify the tremor signal and the contraction-relaxation signal, and output the amplified signals to the detector;
a state analyzing unit configured to determine: (1) whether an average level of an amplitude of the amplified tremor signal is greater than or equal to a first threshold, and (2) whether an average change amount of the amplified contraction-relaxation signal is less than a second threshold value;
a detector configured to detect that the tendon or the muscle is the state that isometric contraction is occurring and isotonic contraction is not occurring when the average level of the amplitude of the amplified tremor signal is greater than or equal to the first threshold and the average change amount of the amplified contraction-relaxation signal is less than the second threshold value; and
a connection terminal that is disposed on a side of the thin signal processing circuit module that is opposite to the flat-film shaped piezoelectric sensor and couples the thin signal processing circuit module to the detector.

* * * * *